United States Patent [19]

Monagan

[11] Patent Number: 5,601,786
[45] Date of Patent: Feb. 11, 1997

[54] AIR PURIFIER

[76] Inventor: Gerald C. Monagan, 14247 Ridge Rd., Albion, N.Y. 14411

[21] Appl. No.: 456,518

[22] Filed: Jun. 1, 1995

Related U.S. Application Data

[63] Continuation-in-part of Ser. No. 252,757, Jun. 2, 1994, abandoned.

[51] Int. Cl.$^6$ ........................................... A61L 9/20
[52] U.S. Cl. ........................... 422/108; 422/119; 422/121; 422/123; 250/437; 250/438; 250/504 R; 55/279; 95/16
[58] Field of Search ........................... 422/4, 24, 120, 422/123, 119, 108, 121; 250/432 R, 435, 437, 438, 504 R; 55/279; 95/8, 11, 12; 96/16

[56] References Cited

U.S. PATENT DOCUMENTS

| | | | |
|---|---|---|---|
| 2,628,083 | 2/1953 | Rense | 261/14 |
| 3,071,828 | 1/1963 | Cornell | 422/121 |
| 3,576,593 | 4/1971 | Cicirello | 422/24 |
| 3,670,193 | 6/1972 | Thorington et al. | 313/112 |
| 3,844,741 | 10/1974 | Dimitrik | 96/16 |
| 4,210,429 | 7/1980 | Golstein | 55/279 |
| 4,468,372 | 8/1984 | Seifert et al. | 42/124 |
| 4,553,992 | 11/1985 | Boissinot et al. | 55/279 |
| 4,621,195 | 11/1986 | Larsson | 250/438 |
| 4,806,768 | 2/1989 | Keutenediian | 250/436 |
| 4,990,311 | 2/1991 | Hirai et al. | 422/4 |
| 5,006,758 | 4/1991 | Gellert et al. | 313/634 |
| 5,019,256 | 5/1991 | Ifill et al. | 210/232 |
| 5,107,687 | 4/1992 | Candeloro | 62/259.1 |
| 5,230,220 | 7/1993 | Kang et al. | 62/78 |
| 5,334,248 | 8/1994 | Kwak | 95/12 |
| 5,337,581 | 8/1994 | Lott | 62/264 |

FOREIGN PATENT DOCUMENTS

| | | | |
|---|---|---|---|
| 3837905A1 | 5/1990 | Germany | 422/24 |
| 2036951 | 7/1980 | United Kingdom . | |
| 2212370 | 7/1989 | United Kingdom | 422/24 |
| 9005909 | 5/1990 | WIPO . | |

OTHER PUBLICATIONS

Light Sources, Inc. Germicidal 1992 Brochure (Technical Bulletin DRS 080592 GER).

*Primary Examiner*—Robert J. Warden
*Assistant Examiner*—Theresa T. Snider
*Attorney, Agent, or Firm*—Lahive & Cockfield; Thomas J. Engellenner; Anthony A. Laurentano

[57] ABSTRACT

A system and method for purifying air by employing a lamp that produces two separate energy intensity maxima. The lamp preferably emits ozone-producing radiation that falls within one wavelength interval, and germicidal radiation that falls within another wavelength interval. The air purifier of the invention includes a housing having an irradiation chamber, an air inlet for introducing air into the irradiation chamber, and a radiation source disposed within the irradiation chamber. The air purifier further includes an air outlet also formed in the housing for discharging the air to an external environment. The method includes providing a housing having an air inlet and an irradiation chamber, and providing a lamp within the chamber wherein the lamp has a relative maximum lamp output within two discrete wavelength intervals. The air is introduced into the irradiation chamber through the air inlet, and the air is irradiated within the chamber. The irradiated air is then discharged from the housing to the external environment. The invention further provides for the utilization of a gas detector to actuate selectively the air purifier of the invention in response to the presence of a selected gas in the air.

21 Claims, 8 Drawing Sheets

AIR PURIFIER

RELATED APPLICATIONS

This application is a continuation-in-part application of U.S. Ser. No. 08/252,757, filed 2 Jun. 1994, entitled Air Purifier, now abandoned.

BACKGROUND OF THE INVENTION

The present invention relates to an air purifying apparatus that destroys microorganisms and removes odors and other impurities from the air.

Today, a large number of pollutants can be found in the air and water. Among the various harmful air pollutants that exist in the air that people breath are pollen, lung damaging dust, smoke and bacteria. Other pollutants include various organic vapors and toxic gases. The environment is often contaminated with a variety of noxious and toxic gases including carbon monoxide, methane, sulphur dioxide, hydrogen sulfide and a broad variety of organic vapors. Some of these are widely prevalent in the environment, particularly in urban areas, and others tend to be pronounced in homes, offices, or other confined spaces due to activities within those spaces. Noxious or toxic materials may be produced from tobacco smoking, cooking, open fireplaces, faulty appliances, or a variety of other normal activities. Some of these are merely unpleasant because of odors while others such as carbon monoxide may be dangerous. Because these pollutants are so prevalent in the air and are found in most locations, contact with them is inevitable. Typically, pollutants cause general discomfort to many people, and can be particularly troublesome to individuals that suffer from emphysema, asthma, and hay fever and like allergies. It has also been found, for example, that a high proportion of homes have unsuspected carbon monoxide concentrations which contribute to vague disorders such as lassitude and headaches at concentrations far below levels that produce overt symptoms of toxicity. Hence, apparatus and methods for removing air pollutants from the air and/or sensing the presence of pollutants have wide spread economic and therapeutic appeal.

Air purifiers are generally known and exist. A typical air purifier includes a housing having a chamber mounting an ultra-violet (UV) lamp. Air is drawn into the bottom of the housing and passes through the chamber where it is exposed to UV radiation emitted from the lamp, which denatures organic proteinous particles, e.g., exterminates microorganisms, that are carried in the air. The air is then discharged from the housing top to the external environment. One prior art air purifier is shown and described in U.S. Pat. No. 4,210,429 of Golstein. The Golstein air purifier employs a UV lamp, which is mounted in a germicidal chamber to exterminate microorganisms that are carried in the incoming flow of air. A charcoal filter is seated above the germicidal chamber and removes odors from the UV radiation exposed air.

Another prior art air purifier is disclosed in U.S. Pat. No. 4,621,195 of Larsson. Larsson also describes an apparatus for destroying microorganisms by irradiation with UV light emitted by a UV lamp supported in an irradiation chamber. The irradiation chamber is segregated into a set of minor chambers by a number of partition walls. The partition walls have formed therein air-flow openings that are oppositely located relative to the openings formed in the adjacent partitions. This alternating arrangement of air-flow openings maximizes the amount of time the air remains in the irradiation chamber in order to maximize the amount of microorganisms destroyed.

There still exists a need in the art for improved air purifiers that can exterminate microorganisms in the air, as well as reduce or eliminate odors. In particular, an air purifier that exhibits improved abilities to exterminate microorganisms while reducing odor emissions would represent a major improvement in the art. Additionally, an air purifier that is relatively compact, relatively easy to manufacture and relatively inexpensive would also present a major improvement in the art.

SUMMARY OF THE INVENTION

The present invention pertains to an air purifier and methods for purifying air employing ultraviolet radiation with two separate energy intensity maxima. The radiation source preferably emits ozone-producing radiation that falls within one wavelength interval, and germicidal radiation that falls within another wavelength interval.

The air purifier of the invention includes a housing having an irradiation chamber, an air inlet for introducing air into the irradiation chamber, and a radiation source disposed within the irradiation chamber. In one aspect of the invention, the radiation source generates a first energy maximum of ozone-producing radiation and a second separate energy maximum of germicidal radiation. The air purifier further includes an air outlet also formed in the housing for discharging the air to an external environment.

According to another aspect, the first energy maximum occurs at a first relative maximum of the total lamp energy output that is in the range between about 160 nm and about 200 nm. The second energy maximum occurs at a second relative maximum of the total lamp output that is in the range between about 230 nm and about 280 nm.

According to further aspects of the invention, the air purifier further includes a heater mounted within the housing that generates heat, a cooling element mounted within the housing for generating and providing to the external environment cool air, and a filter element, mounted within the purifier, for filtering the air.

According to another embodiment of the invention, the air purifier includes a housing element having an irradiation chamber, an air inlet for allowing air to enter into the housing, an air outlet for allowing air to exit the housing, and an air passage element for introducing air into the irradiation chamber and for moving air out of the chamber.

The air purifier can further include a radiation source, mounted within the irradiation chamber, that generates UV radiation having first and second energy maxima that fall within wavelength intervals $\lambda_1$ and $\lambda_2$, respectively. The wavelength interval $\lambda_1$ is in the range between about 230 nm and about 280 nm, and the wavelength interval $\lambda_2$ is in the range between about 160 nm and about 200 nm. The two discrete wavelengths destroy microorganisms carried in the air and substantially simultaneously deodorizes the air.

The present invention further encompasses a system for purifying air. The system includes a housing element having an air inlet, an air outlet, and an irradiation chamber, an air introduction element that introduces air into the irradiation chamber, and a radiation source, mounted within the irradiation chamber, that generates UV radiation having first and second energy maxima within a pair of wavelength intervals. The system further includes a power supply element that supplies power to the air introduction element and the lamp element.

The first energy maximum occurs within the wavelength interval between about 230 nm and about 280 nm, and the second energy maximum occurs within the wavelength interval between about 160 nm and about 200 nm. The two energy maxima destroy microorganisms carried in the air and substantially simultaneously deodorizes the air.

The system can further include a timer element, mounted on the housing, for allowing a user to select a time period in which power is supplied to the lamp. The system can further include a heater, a cooling element, and a filter element, all mounted within the housing.

According to other aspects of the air purifying system, the air introduction means is a blower and the power supply element includes a ballast.

The method of the present invention includes providing a housing having an air inlet and an irradiation chamber, and providing a radiation source within the chamber wherein the source generates a first energy maximum within a first wavelength range of ozone-producing radiation, and generates a second energy maximum within a second wavelength range of germicidal radiation. The first wavelength interval is in the range between about 160 nm and about 200 nm, and the wavelength interval is in the range between about 230 nm and about 280 nm. The two wavelength intervals cooperate to destroy microorganisms carried in the air and substantially simultaneously deodorizes the air.

The method further provides for introducing air into the irradiation chamber through the air inlet, irradiating the inlet air within the chamber, and discharging the irradiated inlet air to an external environment.

The invention further pertains to a gas detection and air purification system that employs an air purifier to remove gas detected by a gas sensor from the external environment. In this embodiment, the purifier can operate in response to an output signal generated by the detector when a selected gas is present in the air.

The air purification and gas removal system of the invention includes a housing having an irradiation chamber, a fan for passing air through the irradiation chamber, and a radiation source that is mounted in the irradiation chamber for irradiating the air passing therethrough. The air preferably resides in the irradiation chamber for a time sufficient to purify the air.

According to one aspect, the system further includes a gas detection element, associated with the housing, for detecting the presence of one or more gases in the air. According to one practice of the invention, the gas detection element generates a gas output signal indicative of the presence of the gas in the air. The gas detection element employed in the present invention can detect the presence of most harmful organic gases, such as carbon oxides, benzene, methane, formaldehyde, sulfur dioxide, oxygen, hydrogen, hydrogen sulfide, $NO_x$, ozone and aerosols, and other harmful and/or toxic vapors including organic vapors.

According to another aspect, the system further includes a power element for selectively supplying power to the housing, and thus to the lamp, in response to the gas output signal. The power element is preferably in electrical communication with the radiation source and the gas detection element.

According to still another aspect of the invention, the radiation source generates radiation within a first wavelength range of ozone-producing radiation and within a second wavelength range of germicidal radiation. The first wavelength range preferably falls within the range between about 160 nm and about 200 nm, and the second wavelength range preferably falls within the range between about 230 nm and about 280 nm.

The invention will next be described in connection with certain preferred embodiments. However, it should be clear that various changes and modifications can be made by those skilled in the art without departing from the spirit and scope of the invention. For example, various housings having differing shapes can be employed to house the lamp.

BRIEF DESCRIPTION OF THE DRAWINGS

The foregoing and other objects, features, aspects and advantages of the invention will be apparent from the following description and apparent from the accompanying drawings, in which like reference characters refer to the same parts throughout the embodiments and different views. The drawings illustrate principles of the invention and, although not to scale, show relative dimensions.

DETAILED DESCRIPTION

Figure 1:
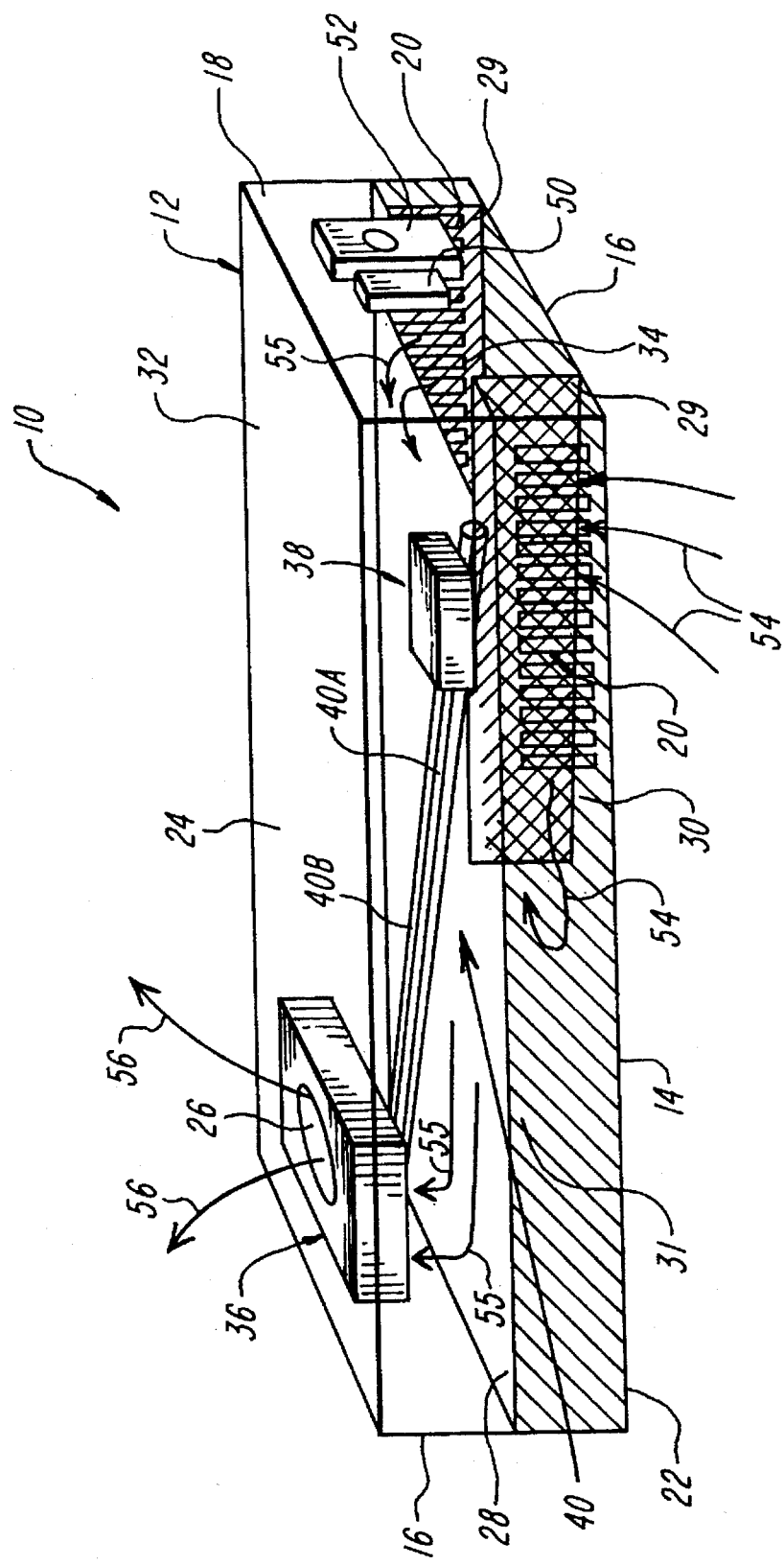
FIG. 1 is a plan view of a first embodiment of an air purifier according to the invention.

FIG. 1 shows an air purifier 10 according to a preferred embodiment of the invention. For purposes of clarity, the internal components of the air purifier throughout the figures are shown. The air purifier 10 includes a housing 12 that has a front wall 14, a pair of sidewalls 16, and a rear wall 18. The front and rear walls 14, 18 have a baffle plate 20 formed thereon. A base 22 supports the front, side and rear walls 14, 16 and 18, and a top cover 24 having an air outlet 26 defining an air outlet passageway encloses the purifier 10.

The housing 12 mounts a substantially horizontal divider plate 28 and a pair of vertically extending shield plates 29. Preferably, the shield plates 29 are spaced from the baffle plates 20 and extend along the front and rear walls a selected distance sufficient to cover the baffle plates 20. The divider plate 28 and the shield plates 29 separate the interior of the housing into an air intake chamber 30, an eradication chamber 31, and an air discharge chamber 32. The shield plate 29 channels the intake air from the intake chamber 30 into the eradication chamber 31, and further provides a barrier between the external environment and the glare of a UV lamp mounted within the purifier, as described below.

The divider plate 28 includes an opening 34 formed at one end of the plate that allows air to flow between the eradication chamber 31 and the air discharge chamber 32. In the illustrated purifier 10, the opening 34 has a substantially rectangular shape. The baffle plates 20 are in fluid communication with the air intake chamber 30, and, in combination, provide an air intake passageway between the external environment and the interior of the purifier.

The air purifier 10 mounts a fan 36 in the air discharge chamber 32. A UV lamp 40 is supported within the eradication chamber 31, beneath the divider plate 28 and is in electrical communication with a lamp power supply 38. The lamp power supply 38, which preferably includes a ballast and a transformer, is a conventional item and is commercially available through Robertson Transformer Co., Ill., U.S.A.

The UV lamp 40 preferably has a pair of contiguous and integrally formed UV radiating sections 40A and 40B. The radiating section 40A preferably produces germicidal radiation within a selected range sufficient to kill microorganisms, such as airborne and surface bacteria, viruses, yeast and molds that are carried in the incoming air. The radiating section 40B preferably produces ozone-generating radiation. As is known, ozone serves as a deodorizer by removing odors from the air, and further functions as a redundant germicidal radiation generator by also producing radiant energy sufficient to destroy microorganisms. The germicidal radiation produced by radiation section 40A further limits the amount of ozone that escapes from the air purifier 10 by reacting with the ozone generated by the radiating section 40B to produce atomic oxygen and oxygen free radicals.

The lamp 40 emits UV radiation having first and second energy maxima. The term "first and second energy maxima" is intended to include the maximum radiation lamp output values, as defined by the total output radiation producing capabilities of the lamp, which occur within selected intervals or range of wavelengths. Preferably, the lamp 40 produces two or more maximum energy values within two or more maximum wavelength intervals. In the illustrated lamp 40, each radiating section 40A, 40B produces at least one energy maximum lamp output value within a selected wavelength range at a selected maximum wavelength. Each maximum energy lamp output value can be either a relative or local maximum value or an absolute maximum value of the total lamp output. Those of ordinary skill will readily recognize that the maximum energy value of the lamp output of each radiating section is a function of the relative size of the radiating section in comparison to the total size of the lamp. For example, the first maximum energy value of the radiating section 40B depends upon the desired amount of ozone-producing radiation to be produced by the lamp. In a preferred embodiment of the invention, the radiating section 40A is three times as large as the radiating section 40B, and thus the maximum output value of section 40A is an absolute maximum, and the maximum output value of section 40B is a relative maximum.

In another aspect of the invention, the air purifier 10 can mount a pair of lamps. Preferably, one lamp produces radiation having a maximum energy value that falls within a first wavelength range, and a second maximum energy value that falls within a second different wavelength range.

Figure 2:
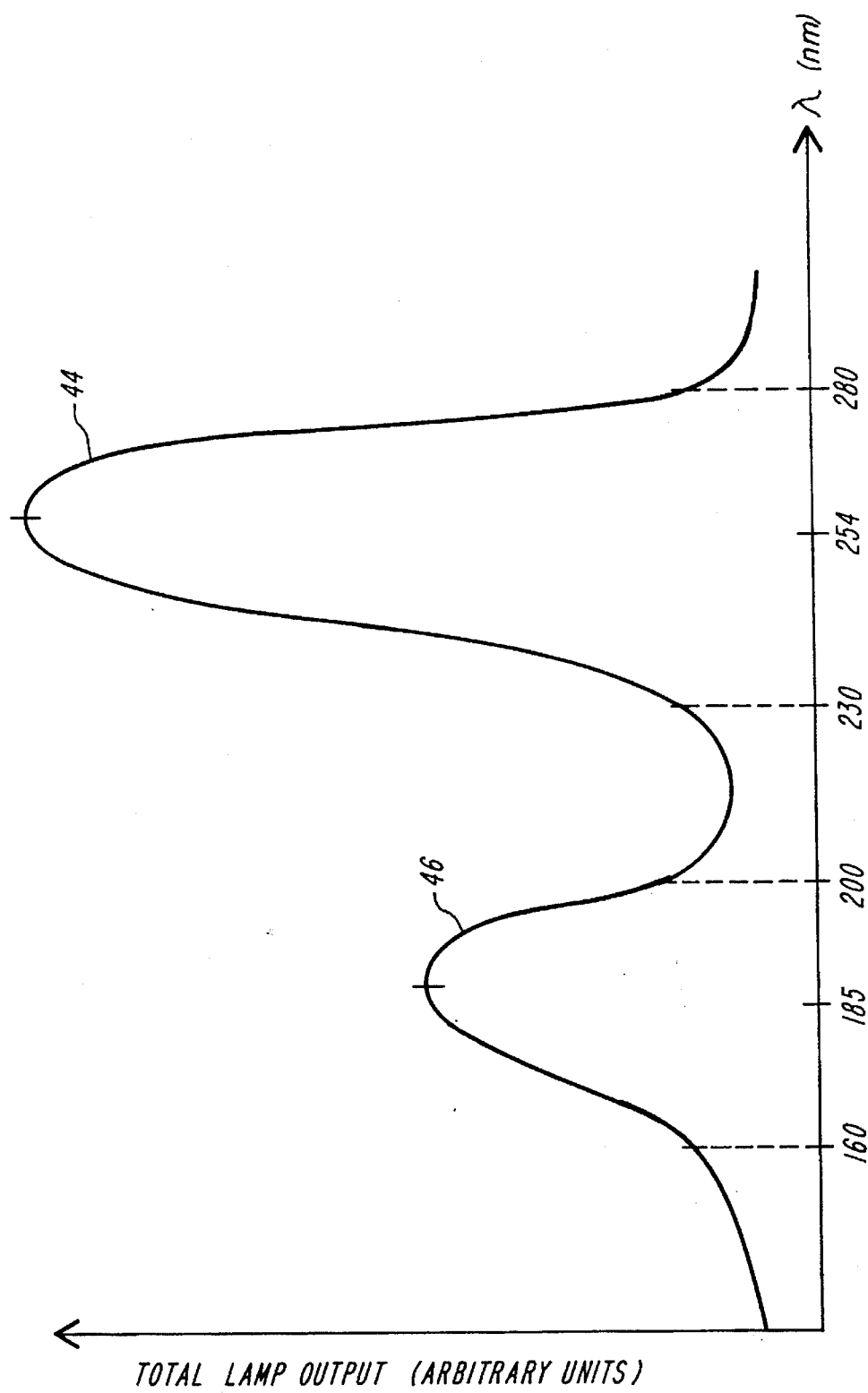
FIG. 2 graphically illustrates the relative maximum wavelengths of radiation produced by the radiation source housed within the air purifier of FIG. 1 according to a preferred embodiment of the invention.

As shown in FIG. 2, the lamp output defined in arbitrary units is plotted against a portion of the wavelength of the total radiation produced by the lamp 40. The radiating sections 40A and 40B, which constitute the radiation producing sections of the lamp 40, produce a pair of wavelength maxima 44 and 46, respectively, within selected wavelength intervals. The first relative maximum lamp output value 46 occurs at or near 185 nm, where the radiating portion 40B preferably emits ozone-producing radiation, within a wavelength range between about 160 nm and about 200 nm. The second maximum output value occurs at or near 254 nm, where the radiating portion 40A preferably emits germicidal radiation, within a wavelength range between about 230 nm and about 280 nm. Those of ordinary skill will readily recognize that the lamp 40 can produce more than two maximum output values by providing a third radiating section that also constitutes a part of the lamp 40. Additionally, other wavelength intervals can be selected depending upon the desired use of the air purifier. The illustrated lamp has a germicidal radiation producing section 40A that is three times larger than the ozone-producing section 40B. This difference in lamp section size is shown by the maximum energy value 44, which is substantially larger than the maximum energy value 46. The preferred lamp 40 is manufactured by Light Sources, Inc., Milford, Conn., U.S.A.

Referring again to FIG. 1, additional features of the air purifier 10 are shown mounted on the sidewall 16. A power switch 50 controls the electrical power supplied to the ballast 38 and thus to the lamp 40. A timer control unit 52 allows a user to select a finite operational time for the air purifier 10, and is commercially available from Pass & Seymour, Syracuse, N.Y., U.S.A.

The lamp 40 can be supported or mounted within the eradication chamber 31 by any suitable means, such as by brackets, and preferably includes a pair of lamp sockets (not shown) that are mounted at either end of the lamp. The sockets are conventional items sold by Light Sources, Inc.

The air flow through the air purifier 10 is generally depicted by the arrows 54, 55 and 56. Specifically, the arrows 54 depict the direction of air flowing into the air purifier and between the air intake chamber 30 and the eradication chamber 31, arrows 55 depict the direction of air flow through the chambers 31 and 32, and arrows 56 depict the direction of air leaving the purifier. During operation of the air purifier, the fan 36 draws inlet air into the air intake chamber 30 through the baffle plates 20 and then into the eradication chamber 31. The air contained within this chamber is then exposed to the UV radiation generated by the lamp 30. This UV radiation preferably has two discrete maximum wavelengths, which serve to destroy microorganisms and to deodorize the air. The air then travels through the opening 34 formed in the divider plate 28 into the air exhaust chamber 32 and is then expelled from the air exhaust chamber 32 by the fan 36 through the air outlet 26.

Figure 3:
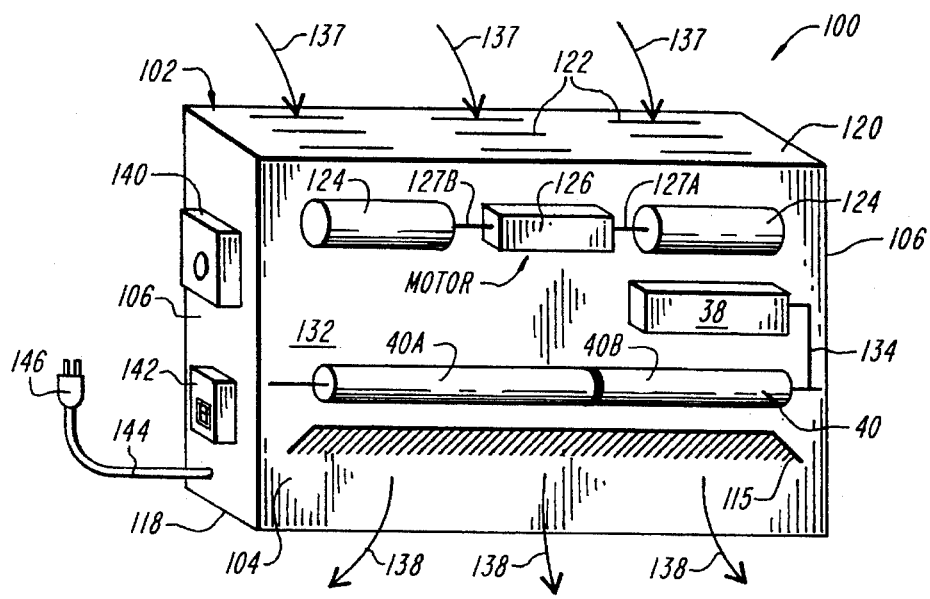
FIG. 3 is a plan view of an air purifier according to a second embodiment of the invention.

FIG. 3 shows an air purifier 100 according to a second embodiment of the invention. The air purifier 100 includes a housing 102 that includes a front wall 104, a pair of sidewalls 106, and a rear wall (not shown). The front wall 104 preferably has a baffle plate 115 formed thereon. A base 118 supports the front and sidewalls 104 and 106 and the rear wall, and a top plate 120 having a plurality of longitudinal slits 122 defining air intake openings encloses purifier 100.

The purifier 100 mounts a pair of blowers 124 that are electrically connected to a motor 126 by electrical leads 127A and 127B. The UV lamp 40 is supported within an irradiation chamber 132 and is connected by way of electrical lead 134 to a lamp power source 38. The UV lamp 40 preferably has a pair of UV radiating sections 40A and 40B that are contiguous and integrally formed, as described above. The radiating section 40A emits UV radiation having a selected germicidal maximum wavelength and radiating section 40B emits UV radiation having a selected ozone-producing maximum wavelength. The lamp 40 can be supported within the housing by a variety of fastening means, such as brackets, and preferably includes a pair of lamp sockets (not shown) mounted at either end of the lamp. The lamp sockets are conventional items and are commercially available from Light Sources, Inc. The blowers 24,24 and the motor 26 are also conventional and commercially available.

Referring again to FIG. 3, additional features of the air purifier 100 are shown mounted on the sidewall 106. A timer 140 mounted on the uppermost portion of the sidewall allows a user to select a finite operational time of the air purifier 100. A power switch 142 mounted beneath the timer controls the power supplied to the purifier. The electrical cord 144, which is connected to the bottom-most portion of the sidewall 106, and the associated plug 146 connect to a conventional 120 volt AC outlet. Alternatively, the plug 146 and the cord 144 can be connected to a 12 V/24 V DC power source, with slight modifications to the ballast, as is known by those of ordinary skill.

The air flow through the air purifier 100 is generally depicted by the arrows 137 and 138. Specifically, the arrows 137 depict the direction of air flow into the air purifier 100, and the arrows 138 depict the direction of flow of the outlet air. In operation, the blowers 124 draw inlet air into the irradiation chamber 132 of the purifier 100 through longitudinal slits 122. The air contained within the chamber is then exposed to selected levels of UV radiation emitted by the lamp 40. This radiation preferably has two discrete selected maximum wavelength ranges, which serve to destroy microorganisms and deodorize the air. The irradiated air is then discharged from the chamber 132 by the blower 124 through the baffle plate 115.

Figure 4:
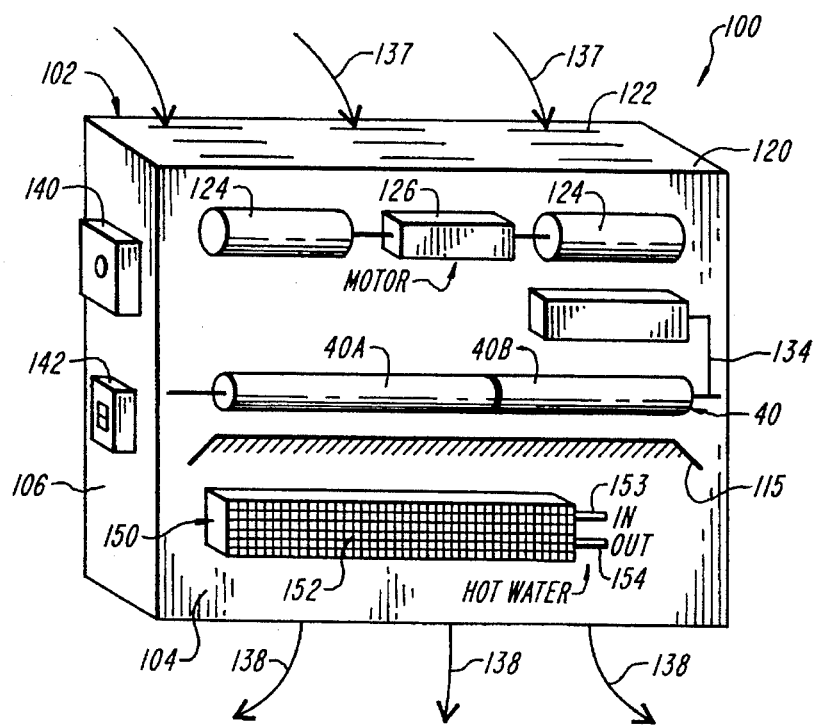
FIG. 4 is a plan view of the air purifier of FIG. 2 which mounts a heat exchanger.

The air purifier 100 can further include a heat exchanger 150, as shown in FIG. 4. The heat exchanger 150 is preferably disposed in the bottom-most portion of the purifier 100, beneath the lamp 40. The heat exchanger 150 has a main body portion 152 that mounts a heating coil (not shown), and has an inlet pipe 153 and an outlet pipe 154. Both pipes 153,154 are connected to an external water source. The inlet pipe 153 transports hot water from the water source to the heating coil, and the outlet pipe 154 functions as the water returns. Thus, in the illustrated embodiment, the air purifier 100, in addition to purifying air, can function as a heater by providing heat to the external environment.

Figure 5:
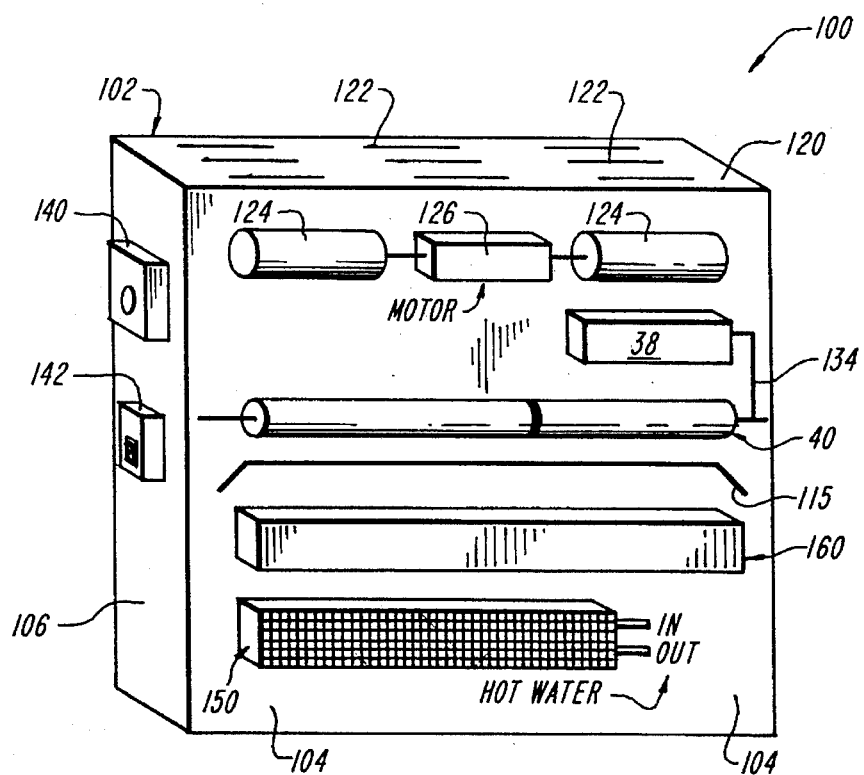
FIG. 5 is a plan view of the air purifier of FIG. 3 which mounts an air conditioning condenser.

As shown in FIG. 5, an air conditioning condenser 160 can also be mounted within the housing 102. The illustrated condenser 160 can be supported within the housing by any suitable fastening means, such as by a bracket. The condenser 160 allows the air purifier to cool the surrounding ambient environment. The illustrated air purifier thus provides a versatile and relatively compact multi-functional unit that heats or cools the surrounding environment, as well as purify the surrounding air.

Figure 6:
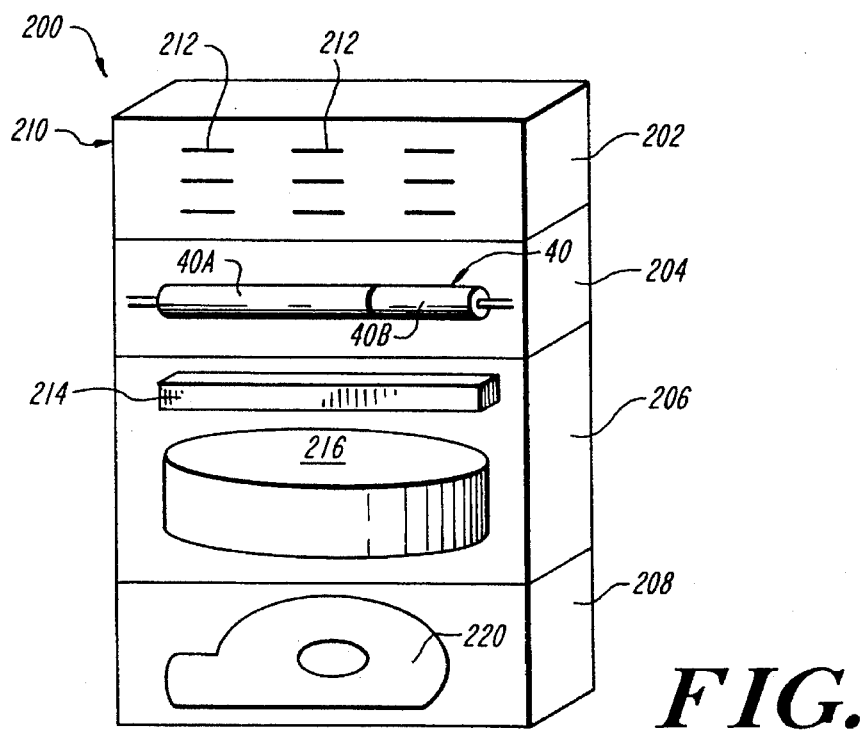
FIG. 6 is a plan view of a third embodiment of an air purifier according to the invention.

FIG. 6 shows an air purifier 200 according to another embodiment of the invention. The illustrated air purifier constitutes a series of stacked compartments or cells 202 through 208. The cells can be secured together to form a unitary housing 210, and each cell is preferably in fluid communication with each other. The uppermost cell 202 preferably is apertured with a series of longitudinal slits 212 forming air inlet passageways. The cell 204 mounts the lamp 40 and forms an irradiation chamber for exposing the incoming air to the germicidal and ozone-producing radiation of the lamp 40.

The third cell 206 preferably mounts one or more, and most preferably two, filters 214 and 216, as shown. The filter 216 is a conventional particulate filter element that may be purchased from Hepa Corporation, Anaheim, Calif., U.S.A. A typical filter comprises a plurality of corrugated foil sheets and a cross membrane. The filter 214 is preferably a conventional charcoal filter, and is disposed above the filter 216. In combination, the filters 214 and 216 remove dust particles and odors from the air.

The bottom-most cell 208 preferably mounts a blower 220. The blower draws air into the multi-stacked air purifier through the air inlets 212 and discharges the air through air outlets formed in the bottom cell 208.

In one particular application of this air purifier, among others, the purifier can be connected to the cold air return of the central heating or cooling system of a residential or commercial air circulation system. Thus, the air purifier can continuously filter and purify the air recirculating in the system.

A significant advantage of the present invention is that the lamp 40 mounted within the air purifier produces a maximum radiation output within at least two separate and discrete wavelength intervals. Those of ordinary skill will recognize that other embodiments of the inventive air purifier can be attained by varying the geometric shape and arrangement of the housing. Moreover, those of ordinary skill will recognize that a pair of lamps can be employed where each lamp produces one absolute maximum lamp output value within a selected wavelength interval.

Figure 7:
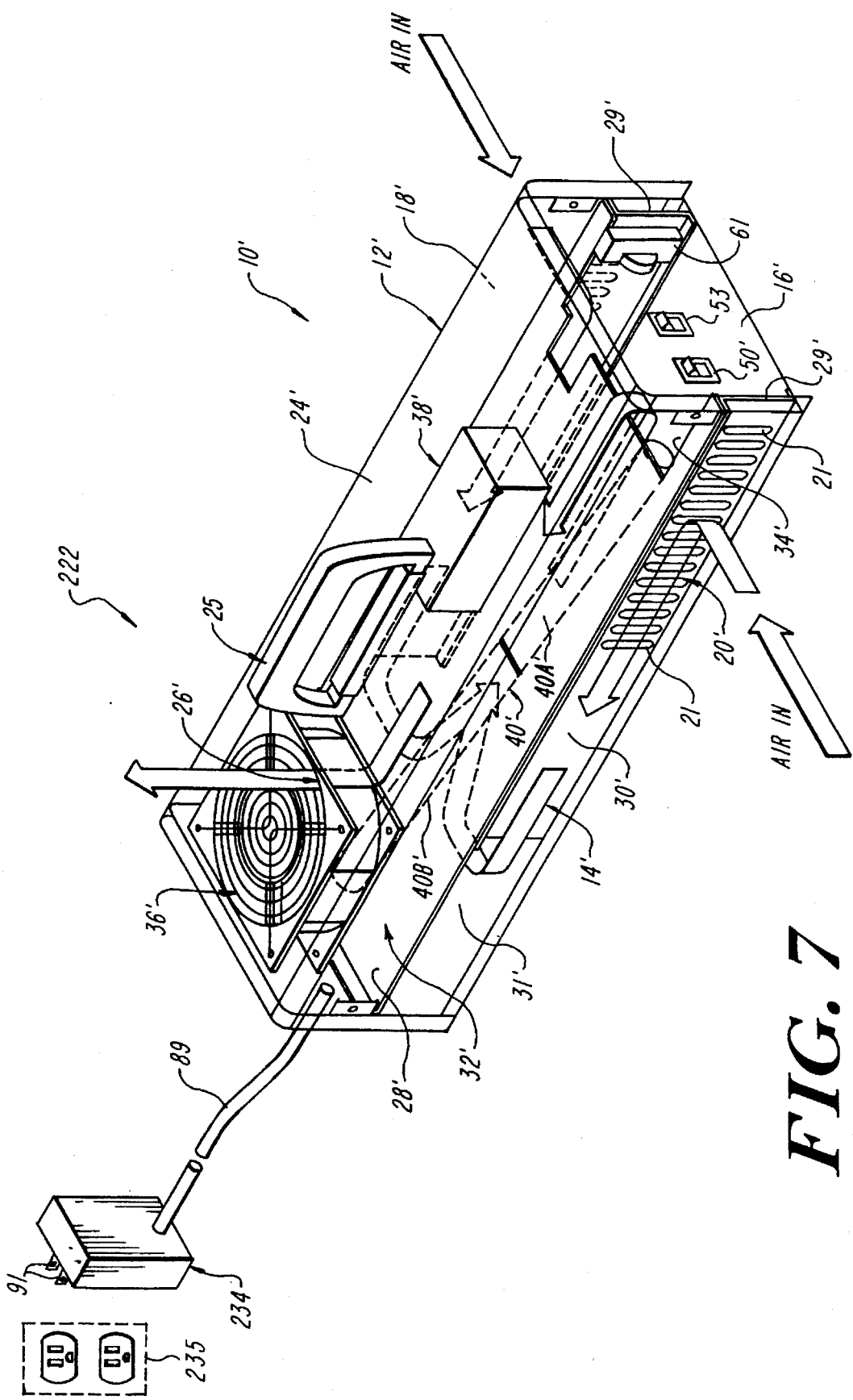
FIG. 7 is a plan view of an air purifying and gas detection system in accordance with the present invention.

According to another feature of the invention, the air purifiers illustrated in FIGS. 1 and 3 through 6 can be integrated with, or connected to, a pollutant or gas detector which detects the presence of one or more types of gas. As illustrated in FIG. 7, the air purifier of FIG. 1 is coupled to a gas detector 234 to form an air purification and gas detection system 222. Elements of the illustrated air purifier that are common and similar to the elements of the air purifier of FIG. 1 are designated with like reference numerals plus a superscript prime. The illustrated air purifier 10' includes a housing 12' that has a front wall 14' and a rear wall 18'. A set of baffle plates 20' having a plurality of vertical slots 21 are formed in the front and rear walls. A top cover 24' mounts a handle 25 and has an air outlet 26' formed therein. A fan 36' is mounted in the air outlet passageway 26' to simultaneously draw air into the air purifier and discharge irradiated air therethrough to the external environment.

As previously described, the housing 12' mounts a divider plate 28' and a pair of vertically extending and axially elongated shield plates 29'. The illustrated shield plates 29' are spaced from the baffle plates 20' formed in wall 14' and extend axially along the front and rear walls a selected distance sufficient to cover the slots of the baffle plates 20'. The divider plate 28' and the shield plates 29' separate the interior of the housing 12' into an air intake chamber 30', an irradiation or eradication chamber 31', and an air discharge chamber 32'. As illustrated, the shield plate 29' channels the intake air from the intake chamber 30' into the eradication chamber 31' and further provides a barrier between the external environment and the glare of a UV lamp 40' mounted within the purifier, as described below.

Referring again to FIG. 7, the illustrated divider plate 28' includes an opening 34' formed at one end, e.g., at the end opposite the fan, that allows air to flow between the eradication chamber 31' and the air discharge chamber 32'.

A UV lamp 40' is supported within the eradication chamber 31', illustrated as beneath the divider plate 28', and is electrically connected to a lamp power supply 38'. The power supply 38' preferably includes a ballast and a transformer. The illustrated lamp 40' is identical to the lamp described above in relation to FIGS. 1 and 2, and preferably has a pair of contiguous and integrally formed UV radiating sections 40A' and 40B'. The lamp 40' can be supported or mounted within the eradication chamber 31' by any suitable means, such as by brackets or other like fastening mechanisms.

The illustrated lamp power supply 38' is electrically coupled via one or more electrical conductors with a power switch 50' that is mounted on sidewall 16' of the illustrated air purifier. The power switch 50' controls the power supplied to the ballast 38' from an external power source, and thus to the lamp 40'. A timer control unit 61 is mounted to one of the baffle plates 20'. and is also electrically coupled to the power supply 38' via electrical conductors (not shown) and to a timer control switch 53 mounted adjacent the power switch 50' on the sidewall 16'. The timer switch in conjunction with the timer control 61 allows a user to select a finite operational time for the air purifier 10'.

An external power source 235 supplies power via a power cord 89 to the air purifier 10'. The illustrated power cord is preferably coupled to the lamp power supply 38' via separate electrical conductors (not shown).

Referring again to FIG. 7, the illustrated gas detector 234 is preferably mounted between the external power source 235 and the air purifier 10' and is directly coupled to the power cord 89. The gas detector 234 can be any conventional gas detector of the type compatible for use with the present invention, and which can detect a variety of gases, such as carbon oxides, e.g., carbon monoxide and carbon dioxide, hydrogen, oxygen, ethanol, propane, butane, methane, formaldehyde, sulphur dioxide, hydrogen sulfide, $NO_x$, ozone, benzene, radon, and aerosols and other toxic or health threatening gases or vapors including a broad variety of organic vapors. In the illustrated embodiment, the gas detector includes a pair of electrical adaptors 91 that are arranged for insertion into a pair of corresponding electrical apertures of the type typically formed in a conventional wall outlet 235. Gas detectors of the type shown and described are available from several manufacturers, including Pama Electronics Co. Ltd., Oceanside, N.Y., U.S.A. According to one practice of the invention, the gas detector senses the presence of a selected gas in the surrounding air. If the detected level of gas is above a selected level, which can be predetermined or selected according to the exigencies of the situation and/or the particular mode of operation of the detector, the detector 234 generates an output signal indicative of the presence of the excess quantities of the selected gas. The detector 234 can also actuate an audible alarm and/or a visual alarm to alert an occupant of the presence of the gas.

In operation, and as illustrated by the block arrows illustrated in FIG. 7, air flows into the air purifier 10' through the baffle plate slots 21 and travels between the front panel 14' and the shield plate 29 which define the air intake chamber 30'. The air is drawn into the air purifier by the operation of the fan 36'. The air then flows from the air intake chamber 30' into the eradication chamber 31' where it is exposed to UV radiation emitted by the lamp 40'. The irradiated air then travels through the opening 34' formed in the divider plate 28' and into the air exhaust chamber 32', where it is expelled through the air exhaust passageway 26' by the fan 36'.

Additionally, the integrated gas detector 234 selectively actuates the air purifier 10' to remove or reduce the levels of selected contaminants e.g., one or more gases, from the surrounding air. For example, if the gas detector senses the presence of a selected gas in concentrations (typically measured in parts per million (ppm)) above a selected level, the detector generates an output signal that is transferred to the air purifier power supply 38' along power cord 89 and other associated wiring. The output signal generated by the gas detector actuates the air purifier, which in turn purifies the surrounding air for a selected period of time. According to one practice, the gas detector output signal activates the air purifier for a selected time period, e.g., 40 minutes, to remove or reduce the levels of gas in the surrounding air. Concomitantly, the gas detector 234 continues to monitor the levels of gas in the air to ensure that the levels do not remain above a selected level. If the gas levels remain above the selected level, e.g., due to a malfunction in the operation of the air purifier, an audible and/or visual alarm can be activated by the detector, in addition to maintaining, if desired, the operation of the air purifier.

The gas detector and the air purifier can cooperate in a number of ways to effect the necessary removal of pollutants from the air that are sensed by the detector. For example, the ballast circuit can include switching circuitry that activates the lamp in response to the output signal generated by the gas detector.

A significant feature of the present invention is that the integration of the gas detector with the illustrated air purifier forms an automatic and modular gas detection and removal system that continuously or periodically samples the surrounding air for a selected gas and removes the selected gas therefrom when the sensed gas level is beyond a predetermined range.

Figure 8:
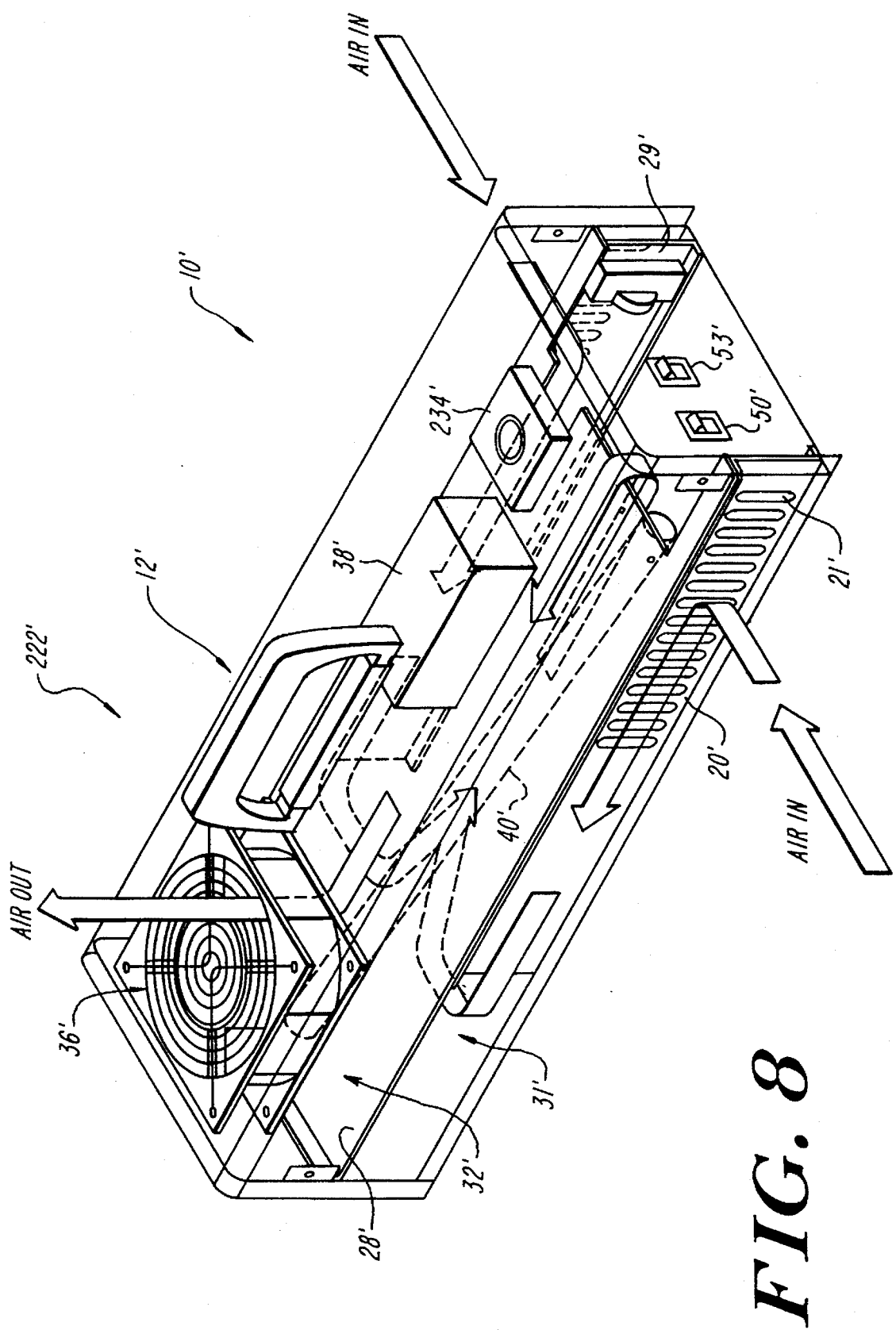
FIG. 8 is a plan view of a second embodiment of the air purifying and gas detection system of FIG. 7.

FIG. 8 shows an alternate embodiment of the air purifier system 222 of FIG. 7. Elements of that system that are common and similar to the elements of the embodiment of FIGS. 1 and 7 are designated with like reference numerals plus a superscript prime. The illustrated system 222 includes an integrated gas detector 234' that is mounted to or on the air purifier housing 12'. Thus, the gas detector need not be adapted for direct insertion into a conventional wall outlet, but rather can be mounted directly to the air purifier unit 10', thus allowing the use of more conventional gas detectors.

The illustrated gas detector can also be coupled with the air purifier via radio frequency electromagnetic waves. According to one practice, the gas detector includes an integrated radio frequency (RF) transmitter. The air purifier has mounted thereon a radio frequency receiver for receiving radio frequency output signals generated by the RF transmitter portion of the detector. During operation, the gas detector generates and emits an RF output signal when the detector senses gas concentrations outside of a predetermined range. The output signal is transmitted as a radio frequency signal and is received by the RF receiver mounted in or on the air purifier. Thus, a gas detector can be remotely located from the air purifier without the necessity of coupling the two with hard wiring.

Figure 9:
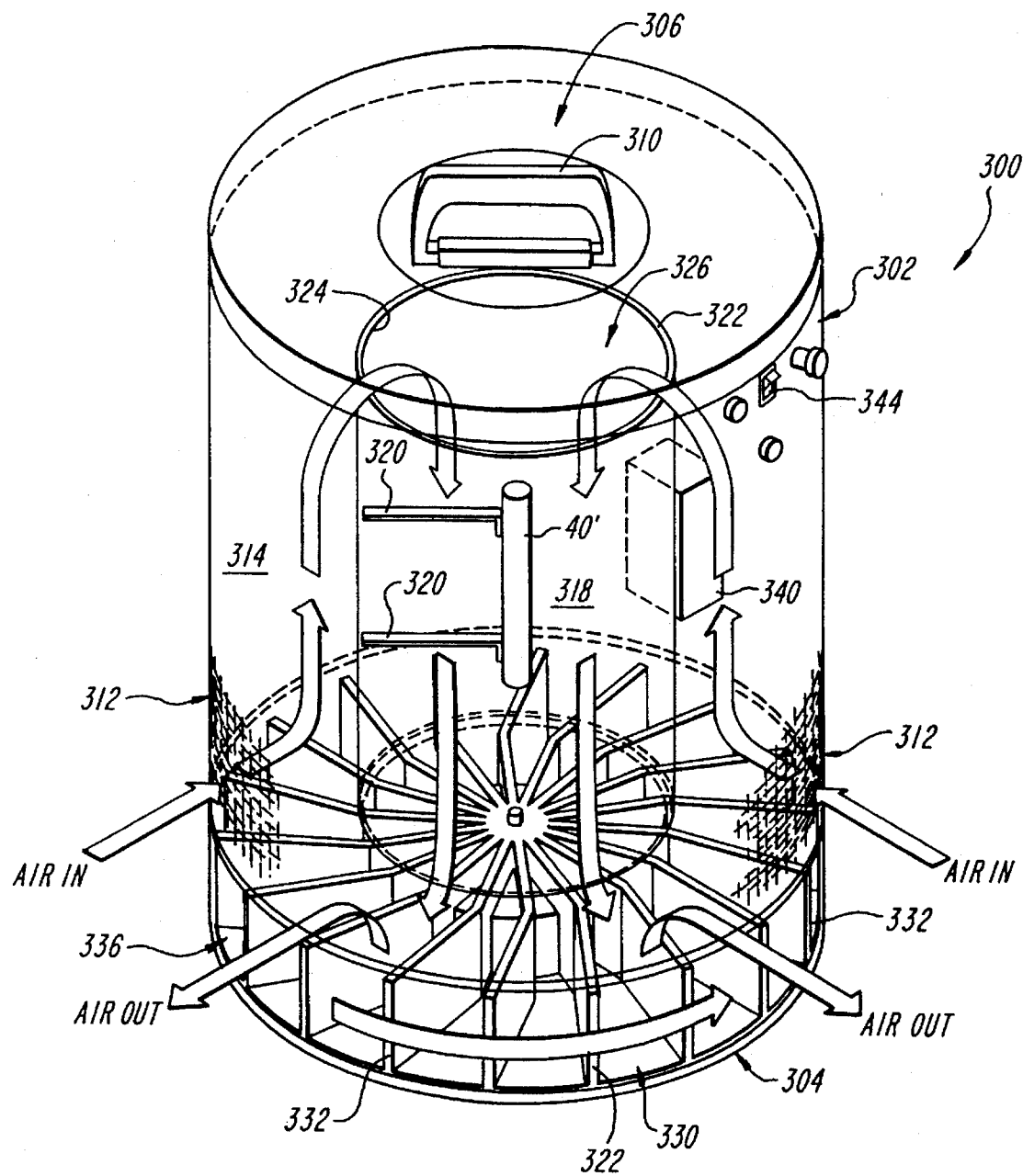
FIG. 9 is a plan view of another embodiment of an air purifying device according to the invention.

FIG. 9 illustrates an alternate embodiment of the air purifier of the invention. The illustrated air purifier 300 is typically employed in commercial environments which require greater quantities of air to be processed and purified. The illustrated air purifier 300 includes a substantially cylindrical housing 302, a bottom portion 304, and a top portion 306. The top portion 306 mounts a handle 310 which assists the user in handling the purifier. The cylindrical housing 302 has formed thereon a plurality of axially spaced rows of apertures 312 defining air inlets, similar to the baffle plates of FIGS. 1 and 7-8. The interior of the purifier mounts a cylindrical divider element 322 that separates the interior of the housing into an air intake chamber 314 and an eradication chamber 318. The illustrated divider 322 has an opening 326 formed in one end that allows air to flow between the inlet passageway 314 and the eradication chamber 318. A UV lamp 40' is supported within the eradication chamber by a pair of support stanchions 320,320 that are coupled to the inner surface 324 of the divider.

A blower 330 is disposed in the bottom portion of the housing 302. The illustrated blower 330 has a plurality of radially extending blades 332 which rotate in a selected manner to draw air into the interior of the air purifier while simultaneously discharging air through an air outlet 336 formed in the bottom of the housing 302. A lamp power supply 340 similar to the power supply 38 of FIGS. 1 and 7-8 provides a selected level of operating power, typically supplied by a conventional wall outlet, to the lamp 40'. The purifier housing 302 has mounted thereon a power switch 344 for controlling the electrical power supply to the ballast 38, and thus to the lamp 40'.

In operation, air is introduced through the air inlets 312,312 by the operation of the blower 330, which is denoted by the block arrows. The air is then carried along the air inlet chamber 314 and into the eradication chamber 318, where the UV lamp irradiates the air for a time sufficient to purify the air. The fan 330 then discharges the irradiated air through the air outlet 336 located in the bottom of the purifier.

Figure 10:
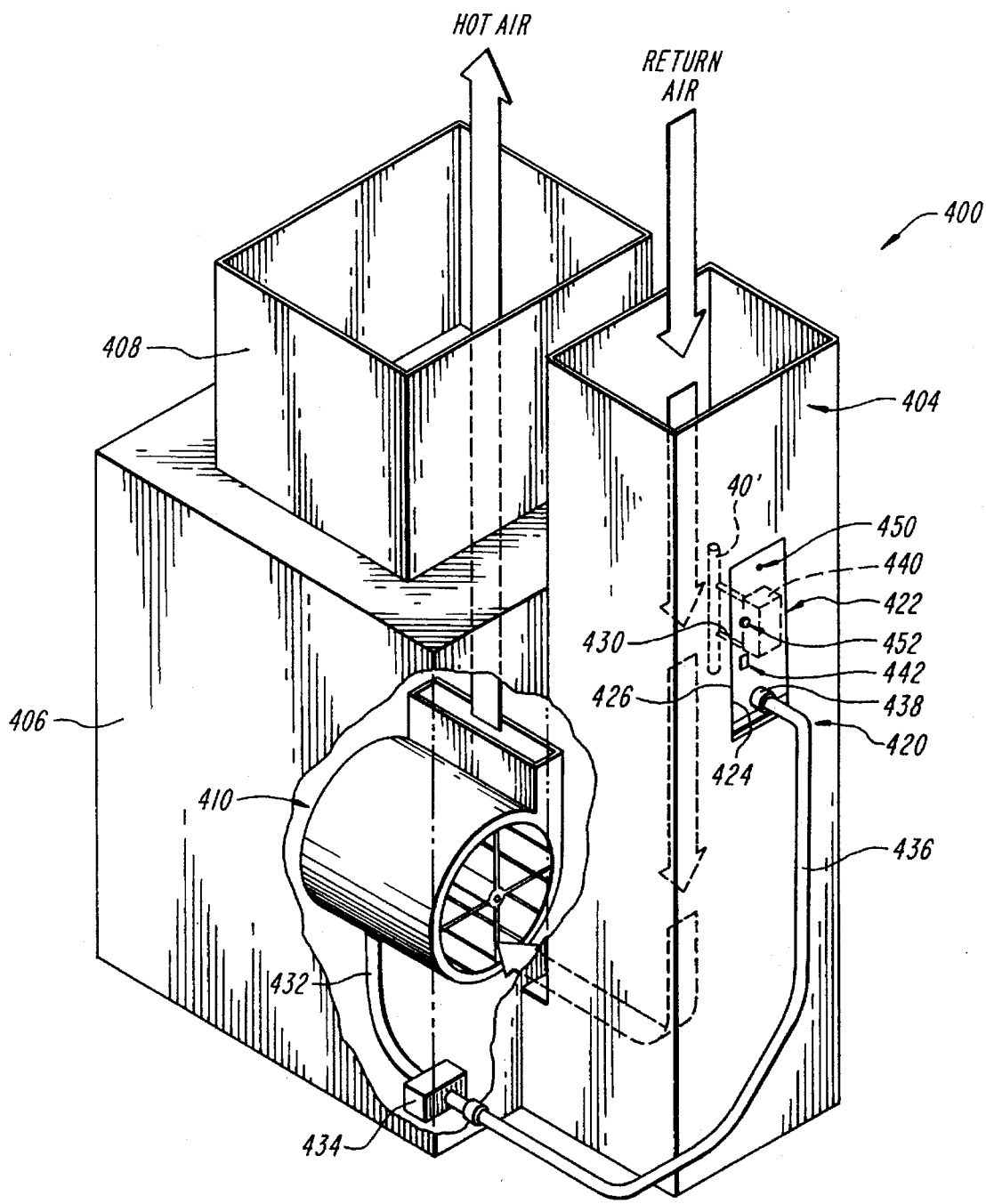
FIG. 10 is a plan view of a third embodiment of the air purifying device according to the invention.

FIG. 10 illustrates another embodiment whereby the air purifying apparatus of the invention is integrated with a heating/ventilation/air conditioning (HVAC) unit. The illustrated HVAC unit 400 can be a conventional heating system that employs a return air duct 404, a furnace portion 406, and a discharge air duct 408. The furnace portion 406 of the HVAC 400 can include a blower unit 410 to heat or cool single or multiple zones in a building structure. The blower unit 410 has an electrical output lead 432 that terminates in a terminal block 434.

The illustrated air purifying device of the invention is mounted in the return air duct 404 of the HVAC unit 400. The air purifying device 420 includes a hinged control panel 422 that has an exposed surface panel 424 and an inner surface 426 that mounts a UV lamp 40' via a pair of support stanchions 430. The illustrated lamp is identical to the lamp previously described. The mounting of lamp 40' inside the return air duct 404 effectively creates an eradication chamber that purifies air passing therethrough.

An electrical power cord 436 is connected electrically in series with the terminal block 434 and the control panel 420. The power cord terminates at a coupling connector 438 formed in the control panel. The lamp 40' and the power cord 436 are coupled via appropriate electrical wiring with an electronic ballast circuit assembly 440 mounted on the inner surface 426 of the panel 420. An electrical power switch 442 functioning as an on/off switch operates the lamp 40' by selectively applying power to the lamp.

The illustrated control panel 420 further includes a sight glass aperture 450 that extends between the exposed and inner surfaces of the control panel 420. The sight glass allows an individual to view the interior of the return duct 404 to check whether the lamp 40' is functioning. A power fuse 452 can further be employed to protect the electronic circuitry associated with the panel 420 and the lamp 40' from overvoltage and/or overcurrent conditions.

In operation, the blower 410 circulates air between the return air duct 404 and the air duct 408, and thus between the HVAC unit and one or more zones within the building. As air is drawn through the return air duct 404, it is irradiated by UV radiation generated and emitted by the lamp 40' mounted therein. The irradiated air exits the return duct 404 and is discharged through the air duct 408 by the blower 410. Thus, the illustrated air purifying device purifies air located in a particular zone of a building.

Those of ordinary skill recognize that a gas sensor can also be integrated with the air purifying device for HVAC units as illustrated in FIG. 10 in accordance with the description set forth in relation to FIGS. 7 and 8. According to one practice, the gas detector can continuously monitor the air flowing throughout the HVAC system to determine if a particular gas is present therein. If so, the gas detector can generate an output signal that actuates the air purification device 420. The operation of the air purifier 420 serves to purify the air passing through the HVAC system by removing or reducing the levels of a particular gas. Optionally, the detector can sound an alarm when the detected gas concentration is greater than a predetermined threshold value or range. In severe situations, the air purification device 420 can turn off the furnace and continuously operate the air purifier, e.g., the UV lamp 40', while actuating the blower unit 410 to continuously circulate air throughout the system. The furnace is then restarted once the levels of the detected gas are within an allowable range of values.

The illustrated lamp can also be mounted in other locations besides the return air duct, such as the discharge duct 408.

Additionally, the commercial air purification embodiment of FIG. 9 can further include a gas detector as described above in relation to FIGS. 7 and 8.

The invention is further illustrated by the following examples, which should not be construed as further limiting.

EXAMPLES

The following examples illustrate the efficacy of the air purifier of the present invention in removing harmful contaminants from the air. The examples were performed under standard conditions, with no introduction of artificial climates or air quality alterations; except for the introduction of a calibrated controlled amount of selected gases to be tested to the ambient environment. The test room was a standard sized room measuring 10 feet by 10 feet.

Example 1

The air purifier of the invention was placed inside the test room and operated for a selected period, such as 24 hours. The air within the room was then sampled using industry approved test equipment, such as the Sensidyne High-Precision Gas Sampling System, which measures over 240 gases. The results of these air measurements are tabulated below in Table 1.

TABLE 1

| Air Purifier Operation Period | Number of Periords Operated | Gas Type Sensed | Concentration (% by volume or ppm) |
| --- | --- | --- | --- |
| 24 hrs. | 3 | $O_2$ | 21.1% |
| 24 hrs. | 3 | HCHO | 0.08 ppm |
| 24 hrs. | 1 | $O_3$ | .013 ppm |

As set forth in Table 1, the operation of the air purifier reduces the levels of contaminants in the air and maintains these levels within acceptable ranges. For example, the oxygen ($O_2$) concentration is maintained within an OHSA acceptable range of 20.5% to 21.5%; the formaldehyde (HCHO) level was maintained below the OHSA level of 0.1 ppm per 24 hours; and the ozone ($O_3$) concentration was below the OHSA acceptable maximum level of 0.05 ppm.

Example 2

The air purifier of the invention was placed inside the test room and the levels of selected gases were measured prior to activation of the air purifier. The purifier was then operated for a selected period of time, and the air inside the test room was again tested to measure the concentration of selected gases using industry approved test equipment. The results of these air measurements are tabulated below in Table 2.

TABLE 2

| Air Purifier Operation Period | No. of Periods Operated | Gas Type Sensed | Prior Concentration | Concentration after Purifier Activated |
|---|---|---|---|---|
| 24 hrs. | 2 | $NO_2$ | 1.5 ppm. | 0.9 ppm |
| 24 hrs. | 2 | $O_2$ | 20.7% by volume | 20.7% |
| 24 hrs. | 2 | CO | 100 ppm | 0.7 ppm |
| 24 hrs. | 2 | $CO_2$ | 1%/hr | 0.8%/hr |
| 24 hrs. | 1 | HCHO | 0.2 ppm | 0.1 ppm |

The air purifier of the present invention reduced the levels of the above gases to within acceptable and safe limits as defined by OHSA.

What is claimed is:

1. An air purification system, comprising
   pollutant detection means for detecting the presence of at least one pollutant in the air, the pollutant detection means being capable of generating a pollutant indicator signal indicative of the presence of the pollutant in the air in quantities above a selected level, and
   a housing having an irradiation chamber,
   means for passing air through the irradiation chamber,
   a radiation source mounted in the irradiation chamber for irradiating the air passing therethrough, and
   power control means in communication with one of said radiation source and said pollutant detection means for selectively supplying power to said radiation source in response to said pollutant indicator signal to actuate said radiation source for a time sufficient to purify the air.

2. The air purification system of claim 1 wherein the radiation source is capable of generating radiation within a first wavelength range of ozone-producing radiation and within a second wavelength range of germicidal radiation.

3. The air purification device of claim 2 wherein the first wavelength range falls within the range between about 160 nm and about 200 nm.

4. The air purification device of claim 2 wherein the second wavelength range falls within the range between about 230 nm and about 280 nm.

5. The air purification system of claim 2 wherein the radiation source is a single UV lamp that generates radiation within both the first and second wavelength ranges.

6. The air purification system of claim 1 wherein the radiation source includes means for generating UV radiation having first and second energy maxima within wavelength intervals $\lambda_1$ and $\lambda_2$, respectively.

7. The air purification system of claim 6 wherein the wavelength interval $\lambda_1$ is in the range between about 230 nm and about 280 nm.

8. The air purification system of claim 6 wherein the wavelength interval $\lambda_2$ is in the range between about 160 nm and about 200 nm.

9. The air purification system of claim 1 wherein the power control means includes a ballast, a source of AC current, and switching means for selectively activating the radiation source in response to the pollutant indicator signal.

10. The air purification system of claim 1 further comprising timer means associated with the power control means for determining a selected time in which power is supplied to the radiation source.

11. The air purification system of claim 1 further comprising a heater mounted within the housing for providing heat to an external environment.

12. The air purification system of claim 1 further comprising cooling means mounted within the housing for cooling an external environment.

13. The air purification system of claim 1 further comprising filter means mounted within the housing for filtering the air passing therethrough.

14. The air purification system of claim 1 wherein the power control means is in electrical communication with the radiation source and the pollutant detection means.

15. The air purification system of claim 1 wherein the pollutant detection means is a pollutant detector.

16. The air purification system of claim 1 wherein the pollutant detection means is capable of detecting the presence of a pollutant selected from the group consisting of carbon monoxide, carbon dioxide, benzene, methane, formaldehyde, sulfur dioxide, oxygen, hydrogen, hydrogen sulfide, $NO_x$, ozone and aerosols.

17. The air purification system of claim 1 wherein the pollutant detection means is capable of detecting carbon oxides.

18. The air purification system of claim 1 wherein the pollutant detection means is capable of detecting benzene.

19. The air purification system of claim 1 wherein the housing having the irradiation chamber comprises the return duct of a HVAC unit.

20. The air purification system of claim 1 wherein said radiation source includes means for generating free oxygen radicals which react with said pollutant.

21. The air purification system of claim 1 wherein said radiation source includes a single UV lamp having both first radiating section means for generating a first energy maximum within a first wavelength range of ozone-producing radiation, and second radiating section means for generating a second energy maximum within a second wavelength range of germicidal radiation, said second radiating section means is about three times larger than said first radiating section means.

* * * * *